United States Patent [19]

Mimura

[11] Patent Number: 5,314,663
[45] Date of Patent: May 24, 1994

[54] AUTOMATIC ANALYSIS APPARATUS FOR CLINICAL EXAMINATION

[75] Inventor: Tomonori Mimura, Ibaraki, Japan

[73] Assignee: Hitachi, Ltd., Tokyo, Japan

[21] Appl. No.: 944,933

[22] Filed: Sep. 15, 1992

[30] Foreign Application Priority Data

Sep. 18, 1991 [JP] Japan .................................. 3-238181

[51] Int. Cl.⁵ .......................................... G01N 35/02
[52] U.S. Cl. ........................................ 422/67; 422/63;
422/64; 422/65; 422/100; 422/102; 422/104;
422/105; 436/43; 436/47; 436/48; 436/49;
436/50; 436/54; 436/55; 436/174; 436/180
[58] Field of Search ..................... 422/67, 63, 64, 65,
422/100, 102, 104, 105; 436/43, 47, 50, 54, 48,
49, 55, 174, 180

[56] References Cited

U.S. PATENT DOCUMENTS

| | | | |
|---|---|---|---|
| 4,612,289 | 9/1986 | Furuta et al. | 436/34 |
| 4,647,432 | 3/1987 | Wakatake | 422/64 |
| 4,675,162 | 6/1987 | Sakamaki et al. | 422/65 |
| 4,939,095 | 7/1990 | Yokotami | 436/47 |
| 5,100,622 | 3/1992 | Minaura et al. | 422/67 |
| 5,176,880 | 1/1993 | Iwasaki et al. | 422/63 |

FOREIGN PATENT DOCUMENTS

| | | |
|---|---|---|
| 041378 | 12/1981 | European Pat. Off. . |
| 273057 | 7/1988 | European Pat. Off. . |
| 316766 | 5/1989 | European Pat. Off. . |
| 359049 | 3/1990 | European Pat. Off. . |
| 409126 | 1/1991 | European Pat. Off. . |
| 3-156372 | 7/1991 | Japan . |
| 88/00704 | 1/1988 | PCT Int'l Appl. . |

Primary Examiner—James C. Housel
Assistant Examiner—Long V. Le
Attorney, Agent, or Firm—Fay, Sharpe, Beall, Fagan, Minnich & McKee

[57] ABSTRACT

An automatic analysis apparatus for clinical examination is capable of performing analytical measurements with improved reliability by suppressing errors of data ascribable to the material of a reaction tube. Plural types of reaction tubes of mutually different materials are so arrayed as to arrive at a sampling position substantially in an alternate manner. In dependence on the item for analysis, the reaction tube of a material compatible with the analytical item is selected from plural types of the reaction tubes to be used for the analysis. The reaction tubes of mutually different materials are accommodated within respective containers. Upon performing the analysis, the reaction tube of the material compatible with the item for analysis is selected by a reaction tube transfer mechanism and set at a position from which the analysis is started, and then analysis is effected.

12 Claims, 8 Drawing Sheets

| ITEM \ MATERIAL OF TUBE | ACRYL | GLASS |
|---|---|---|
| IMMUNE GLOBULIN G | — | O |
| IMMUNE GLOBULIN A | — | O |
| IMMUNE GLOBULIN M | — | O |
| TTT | — | O |
| CHOLESTEROL | — | O |
| TP | O | — |
| ALB | O | — |
| AST | O | — |
| LD | O | — |
| BUN | O | — |

AUTOMATIC ANALYSIS APPARATUS FOR CLINICAL EXAMINATION

BACKGROUND OF THE INVENTION

The present invention relates to an automatic analysis apparatus for performing clinical examinations. More particularly, the invention is concerned with an automatic analysis apparatus which is adapted to perform an analysis for clinical examination by selecting a reaction tube composed of a material to which a reagent does not stick or adhere.

Automatic analysis equipment for clinical examination known heretofore, there may be have included a table for holding samples, a table for holding reagents, a reaction tube into which a sample and a reagent are pipetted, a table for holding a plurality of reaction tubes, a sample pipetting mechanism, a reagent pipetting mechanism, a light intensity measuring instrument for measuring absorbance of a liquid reactant within the reaction tube, a cleaning, mechanism for cleaning the reaction tube, and a computer for controlling operations of the whole system. In operation of the analysis apparatus, a predetermined amount of a sample is pipetted into a reaction tube, followed by pipetting of a predetermined amount of a reagent into the tube, whereupon reaction of the sample with the reagent is conducted. After lapse of a predetermined time, light absorbance of the liquid reactant is measured to analyze concentrations of components of the sample. After completion of the analysis, the used reaction tube is cleaned by the cleaning mechanism for making it reusable in a succeeding analysis. In general, in the automatic analysis apparatus for the clinical examination, the reaction tubes are cleaned after analysis and used repeatedly.

In the automatic analysis apparatus, the reaction tube is often used again for the analysis of an item which differs from that of the preceding analysis or measurement. In that case, when the reagent used for the item subject to the preceding analysis is to be employed in the reaction with a sample concerning the item designated for the succeeding analysis, and when the reagent used in the preceding analysis can not completely be removed from the reaction tube notwithstanding the cleaning performed at the final stage, an error may occur in the data of measurement. Avoidance of such an error relies on the judgement of the clinical examiner. Namely, the phenomenon of adhesion of the reagent to the reaction tube is suppressed to a possible maximum by avoiding the use of the combination of the reagent tube and the sample or reagent which may give rise to the adhesion phenomenon. Further, the analysis for the item which tends to bring about an error or abnormality in the measurement data is usually performed separately after measurements or analyses for all the other items have been completed.

It is also conceivable that some chemical reaction may take place between a reagent and the reaction tube. In that case, the analysis is performed by replacing the concerned reaction tube with a tube made of glass which is intrinsically immune to the chemical reaction. Upon completion of the analysis, the glass tube is cleaned by using a cleaning agent and rinsed with water for reuse in a succeeding analysis.

In the automatic analysis apparatus or equipment, it has been a general practice to use repeatedly a reaction tube made of a plastic material by cleaning it after the analysis for reuse in the succeeding analysis because plastic reaction tubes are expensive. However, when use is limited to plastic reaction tubes, there arises problems that the reagent can not completely be removed solely by the cleaning and that reaction may take place between the plastic tube and the reagent. In case a reagent component adheres fixedly to the reaction tube, the former will partake in the reaction for the succeeding analysis and contribute to color development. Consequently, the reaction rate becomes higher when compared with the case in which the reaction tube as used is utterly free of the sticking reagent, thus incurring erroneous measurement result. Moreover, in the case of a colloidal reaction such as the thymol turbidity test (TTT), for example, the reagent is likely to react with the plastic test tube, causing an error in the resulting data. In this manner, the measurement data made available with the conventional automatic analysis apparatus are susceptible to significant influence of selected combinations of the reaction tube materials and the reagents, incurring errors in the result of the analyses.

In order to avoid the inconveniences mentioned above, it is necessary to replace all of the plastic reaction tubes with tubes made of a material that is insusceptible to reaction with the reagents, as in the case of the thymol turbidity test (TTT). However, such replacement requires additional time, whereby the analysis process is undesirably elongated. Besides, glass tubes are more expensive than plastic tubes, thus involving an increase in the running cost.

Moreover, when the reagent adheres fixedly to the reaction tube, difficulty will be encountered in evading the adverse influence to the succeeding analysis performed by the same tube even when the latter is cleaned sufficiently. Under the circumstances, it will become necessary to limit the items to be analyzed by the apparatus or to select the reagents to be used in dependence on the materials of the reaction tubes.

SUMMARY OF THE INVENTION

It is therefore an object of the present invention to provide an automatic analysis apparatus for clinical examination which can always assure selective use of a reaction tube of a material suited optimally for a reagent to be used in analysis of a sample for a given item designated for analysis.

In view of the above and other objects which will become apparent as the description proceeds, there is provided according to a general aspect of the present invention an automatic analysis apparatus for clinical examination which comprises at least a sample table provided with a plurality of samples, a reagent table equipped with plural types of reagents, a reaction table having a large number of reaction or test tubes disposed thereon for use in reactions between samples and reagents, a sample pipetting unit for pipetting a given one of the samples into a given one of the reaction tubes, a reagent pipetting unit for pipetting a given one of the reagents into the reaction tube having the sample, a mixing mechanism for mixing together the sample and the reagent contained in the reaction tube, a photometer for measuring absorbance of the liquid reactant within the reaction tube, a tube cleaning mechanism for cleaning the reaction tube to remove away the liquid reactant, and control means for controlling operations of the whole apparatus, wherein plural types of reaction tubes of different materials are previously installed on the reaction table before the start of the analysis process, and wherein the reaction tube of the material suited optimally for an item given or designated for analysis is automatically selected.

DESCRIPTION OF THE PREFERRED EMBODIMENTS

In the following, the present invention will be described in detail in conjunction with preferred or exemplary embodiments thereof by reference to the drawings.

Figure 1:
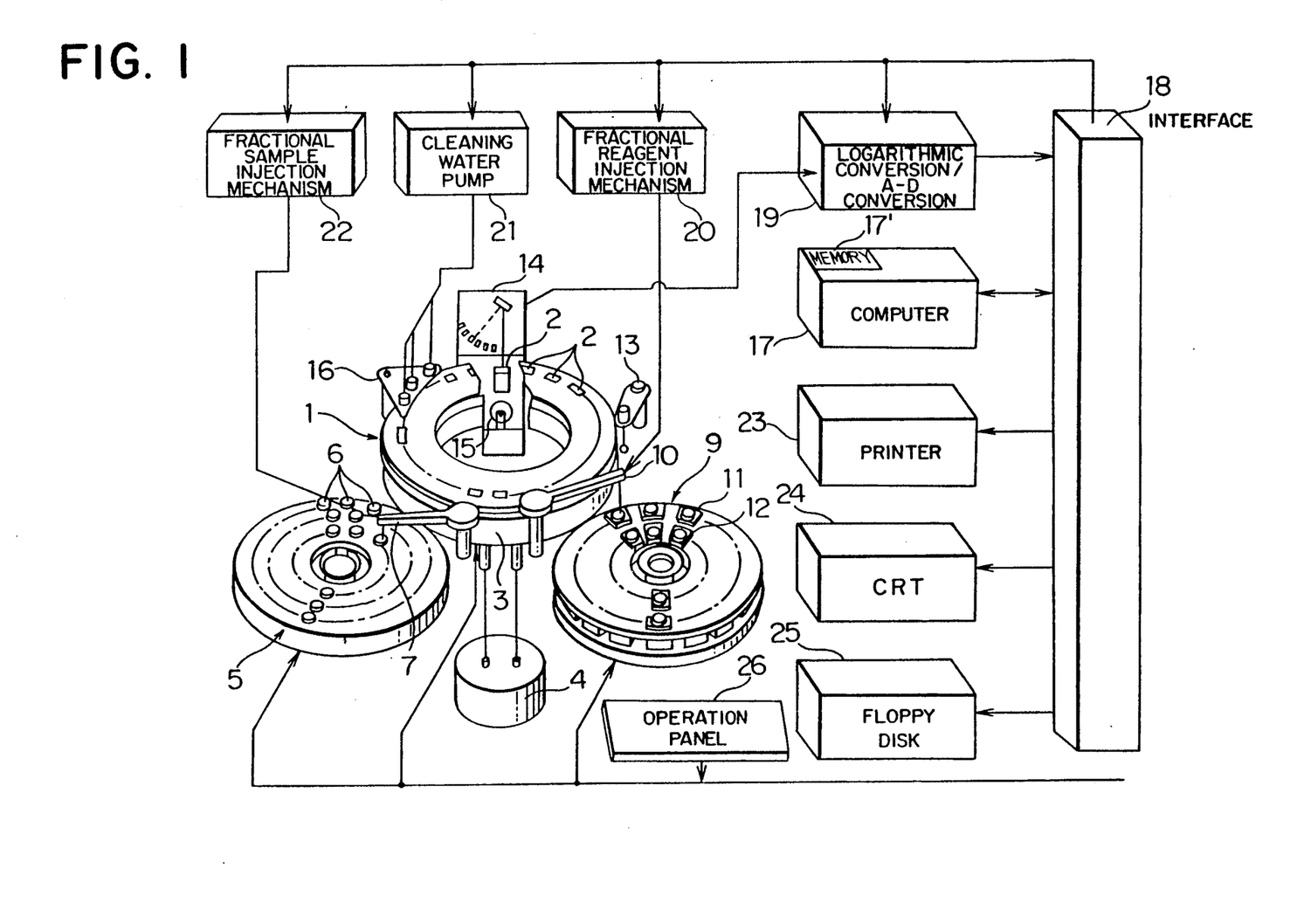
FIG. 1 is a view showing schematically a general structure of an automatic analysis apparatus according to a first embodiment of the invention.

FIG. 1 shows schematically a structure of an automatic analysis apparatus according to an embodiment of the invention. In this figure, reference numeral 1 denotes a disk-like reaction table which is mounted rotatably and adapted to be rotated by a driving mechanism (not shown) installed beneath the reaction table. Rotation of the reaction table 1 by means of the driving mechanism is controlled by a controller which will be described hereinafter. Mounted on the upper surface of the reaction table 1 along the outer peripheral edge thereof are reaction or test tubes 2 which number, for example, 48. The reaction table 1 is immersed in a heat-insulating bath (not shown) whose temperature is maintained at a constant level by a temperature maintaining mechanism generally denoted by reference numeral 4. Thus, the reaction table 1 as a whole is constantly maintained at a predetermined temperature.

Reference numeral 5 denotes a sample table in which a large number of sample cups 6 are disposed. A rotational drive mechanism (not shown) is also installed beneath the sample table 5 so that the latter can be rotated, as occasion requires, under the control of a controller described hereinafter. Samples contained in the sample cups 6 are extracted selectively, as the occasion demands, by means of a tip nozzle of a sample pipetting mechanism 7 to be pipetted into the reaction tube set at a sampling position on the reaction table 1.

Reference numeral 9 denotes a reagent table in which a number of reagent cups are disposed. A reagent pipetting mechanism 10 is provided in association with the reagent table 9. The reagent cups are disposed along duplicate circular paths, i.e. an inner circular path and an outer circular path, wherein the cups 11 for first reagents are disposed along the outer circular path with the cups 12 for second reagents being disposed along the inner path. The reagent pipetting mechanism 10 is adapted to pipette the first and second reagents into a reaction tube containing a sample in a predetermined order under the control of the controller, as described hereinafter.

Reference numeral 13 denotes a mixing mechanism disposed adjacent to the reagent table 9. The mixing mechanism 13 mixes the contents of a reaction tube containing the sample and the reagents pipetted therein, to thereby set up a reaction liquid state in which reaction easily takes place.

Reference numeral 14 denotes a multiwave-length photometer and 15 denotes a light source. A light beam emitted from the light source 15 is directed toward the multiwavelength photometer 14. The reaction tube 2 containing the object for photometry is caused to move and pass between the multiwavelength photometer 14 and the light source 15. When the light beam projected from the light source 15 is cross by the reaction tube 2, light intensity associated with the reaction liquid contained in the reaction tube is measured by the multiwavelength photometer 14. Reference numeral 16 denotes a cleaning mechanism which is adapted to clean the interior of the reaction tube after the photometry.

Now, description will turn to a control system and a signal processing system. In FIG. 1, reference numeral 17 denotes a computer, 18 denotes an interface, 19 denotes a logarithmic conversion/analog-to-digital (A/D) conversion unit, 20 denotes a fractional reagent injection system, 21 denotes a cleaning water pump and reference numeral 22 denotes a fractional sample injection system. Further, there are provided a printer 23, a cathode ray tube (CRT) 24, a floppy disk drive 25 serving as a storage unit and an operation or manipulation panel 26 through which an operator can input information concerning the analysis. The fractional reagent injection mechanism 10 and the reagent pipetting mechanism 20 constitute a reagent injection system while the sample pipetting mechanism 7 and the sample injection mechanism 22 constitute a sample injection system.

In the system arrangement shown in FIG. 1, the operator of the automatic analysis apparatus inputs analysis request information (items for the analysis) through manipulation of the operation panel 26 upon starting of an analysis process. The, analysis request information is stored in a memory 17' incorporated in the computer 17. Subsequently, the operator places a sample in the sample cup 6 located at a predetermined position on the sample table 5. Meanwhile, the reaction tubes 2 which are disposed on the reaction table 1 along the outer periphery thereof and which are to be employed for the reaction are cleaned once per machine cycle by using ion-exchange water supplied from the cleaning water pump 21 through the cleaning mechanism 16. The cleaning ion-exchange water injected through the cleaning mechanism 16 is discharged through a vacuum pump (not shown) every time the cleaning has been completed.

Figure 2:
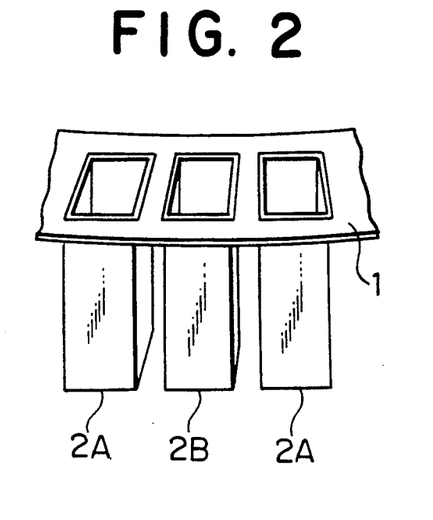
FIG. 2 is a schematic view showing partially an array of reaction tubes of different materials disposed on a reaction table.

On the reaction table 1, there are provided two types of reaction tubes which differ from each other in material. More specifically, 24 reaction tubes 2A each made of an acrylic resin and 24 reaction tubes 2B each made of glass are arrayed alternately, as is illustrated in FIG. 2. On the other hand, the reagent table 9 is provided with 20 items or types of first reagents 11 and 20 items or types of second reagents 12.

Upon starting of the analysis, the reaction table 1 is rotated one complete revolution plus an angular distance corresponding to the distance between two adjacent reaction tubes (i.e., the inter-tube angular distance) during a period, say, of 24 seconds. When the reaction tube of concern stops at a sampling position, a sample for the item to be analyzed by using that reaction tube is pipetted into that tube in a predetermined amount by the sample pipetting mechanism 7. Subsequently, the reaction table makes one complete rotation to stop at a position for pouring the first reagent 11 by the reagent pipetting mechanism 10.

Subsequently, the reaction table 1 is rotated continuously for a period of 15 cycles, where one cycle corresponds to one complete rotation plus one inter-tube angular distance to ensure a time period (24 seconds ×15) required for the reaction. After lapse of this time period, the reaction table stops at the position for pipetting the second reagent 12, again by the reagent pipetting mechanism 10. After completion of injection of the sample and the first and second reagents, the reaction table 1 is again rotated for a period of fifteen cycles.

In the course of the sequential operations described above, the reaction tube containing the sample and the added reagents which are sufficiently mixed together by the mixer passes by the multiwave-length photometer 14, whereby the absorbance exhibited by the liquid reactant for a variety of wavelengths, are respectively automatically measured. The data obtained from the measurement are inputted to the computer 17 via the logarithmic and A/D conversion unit 19 and the interface 18. The computer 17 processes and converts the absorbance data as measured into concentration data. After completion of the analysis, the reaction tube 2 is cleaned by the ion-exchange water supplied from the cleaning water pump 21 through the reaction tube cleaning mechanism 16 for subsequent use. An automatic analysis apparatus of similar structure and operations outlined above is disclosed in U.S. Pat. No. 4,612,289.

Figure 3:
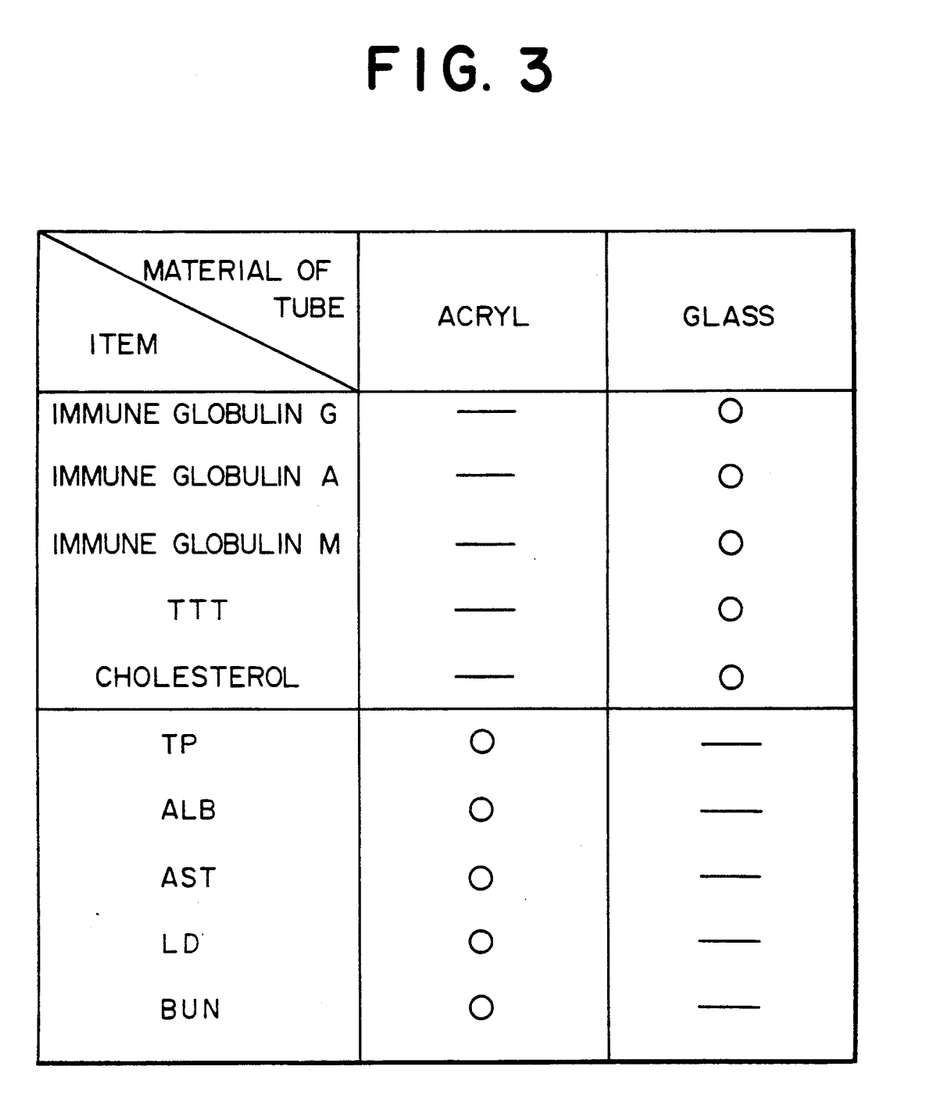
FIG. 3 shows a list indicating correspondence or compatibility relations between items for analysis and materials of reaction tubes.

Since the reaction tube 2A of acrylic resin and the reaction tube 2B of glass are alternately disposed on the reaction table 1, the reaction tubes 2A and 2B of different materials arrive alternately at the sampling position. The sample which is to be analyzed is pipetted into the reaction tube when it arrives at the sampling position. In precedence to the pipetting of the sample and the start of analysis, a table or list indicating compatibility relations between the items for analysis and the material of the reaction tubes as illustrated in FIG. 3 is stored in the memory 17' incorporated in the computer 17. Upon arrival of the reaction tube at the sampling position, the computer 17 consults the above-mentioned table to check the compatibility or affinity between the material of the reaction tube located at the sampling position and the item for the analysis to thereby determine the possibility of occurrence of an adhesion problem as mentioned hereinbefore. When it is determined that adhesion may possibly take place between the material of the test or reaction tube and the reagent for the item selected for the analysis, the pipetting of the sample into the reaction tube located at the sampling position is suspended. In this manner, the analysis procedure is so controlled that when there arises the problem of adhesion between the material of the reaction tube used for the analysis and the item for the analysis, the sampling is temporarily suspended to wait for arrival of the reaction tube of another material, whereupon the sampling is performed.

In practice, the problem of adhesion between the material of the reaction tube and the reagent for the item for analysis may take place in the case where a reaction tube 2A of a plastic material such as acrylic resin is set at the sampling position. By way of example, lipoprotein lipase (enzyme) contained in a cholesterol measuring reagent will fixedly adhere to the inner wall of the reaction tube of acrylic resin and cannot be removed by cleaning with water. Accordingly, when items related to a lipid, such as those typified by free cholesterol, free fatty acids or the like are to be measured, progress of the reaction tends to be promoted by lipoprotein lipase adhering to the wall of the reaction tube, as a result of which a greater value of the measurement of lipid will be obtained when compared with the inherent value (i.e. value of measurement which will be obtained from the reaction when it is performed in the absence of lipoprotein lipase). In contrast, in the case of a reaction or test tube of glass, no lipoprotein lipase can adhere to the inner wall of the tube, which means that the measurement does not assume a value greater than the intrinsic one.

Parenthetically, in FIG. 3, TP represents total protein, ALB represents albumin, AST represents aminotransferase, LD represents lactate dehydrogenase and BUN represents urea nitrogen.

In the automatic analysis apparatus according to the instant embodiment of the invention, the computer 17 is used as the control facility, wherein the relations concerning the adhesion between the reagents and the reaction tubes are previously stored in,.the memory 17' incorporated in the computer. Further, items for analysis are registered in the computer in correspondence to the respective samples.

In the case of the analysis apparatus having the reaction table load with a large number of reaction tubes, the reaction table is rotated at a predetermined time interval, say, at an interval of 24 seconds, in the manner described previously, whereby the reaction tubes are caused to stop at the sampling position by turns and by rotation. The computer which stores the data concerning the materials of the reaction tubes installed on the reaction table checks the relation or compatibility between the material of the reaction tube and the reagent for the item for analysis to thereby determine the reagent for the analysis which involves no problem in the analysis. It should be recalled that the reaction tubes of different materials are alternately arrayed on the reaction table in such a sequence that after lapse of one cycle, the reaction tube of another material can arrive at the sampling position. Again, the computer checks the compatibility of this reaction tube through the procedure mentioned above.

The reaction tube which has passed this check is fractionally poured with the sample for the analysis at the sampling position. Subsequently, at least a first reagent is injected in this reaction tube after lapse of a predetermined time. In the course of rotation of the reaction table, absorbance of the liquid mixture within the reaction tube is measured, and the computer arithmetically determines the corresponding concentrations. Thereafter, the reaction tubes are cleaned in preparation for a succeeding analysis. In this way, the influence of the reagent chemicals on the reaction tube can be suppressed to a minimum, ensuring availability of measurement data with high accuracy.

Figure 4:
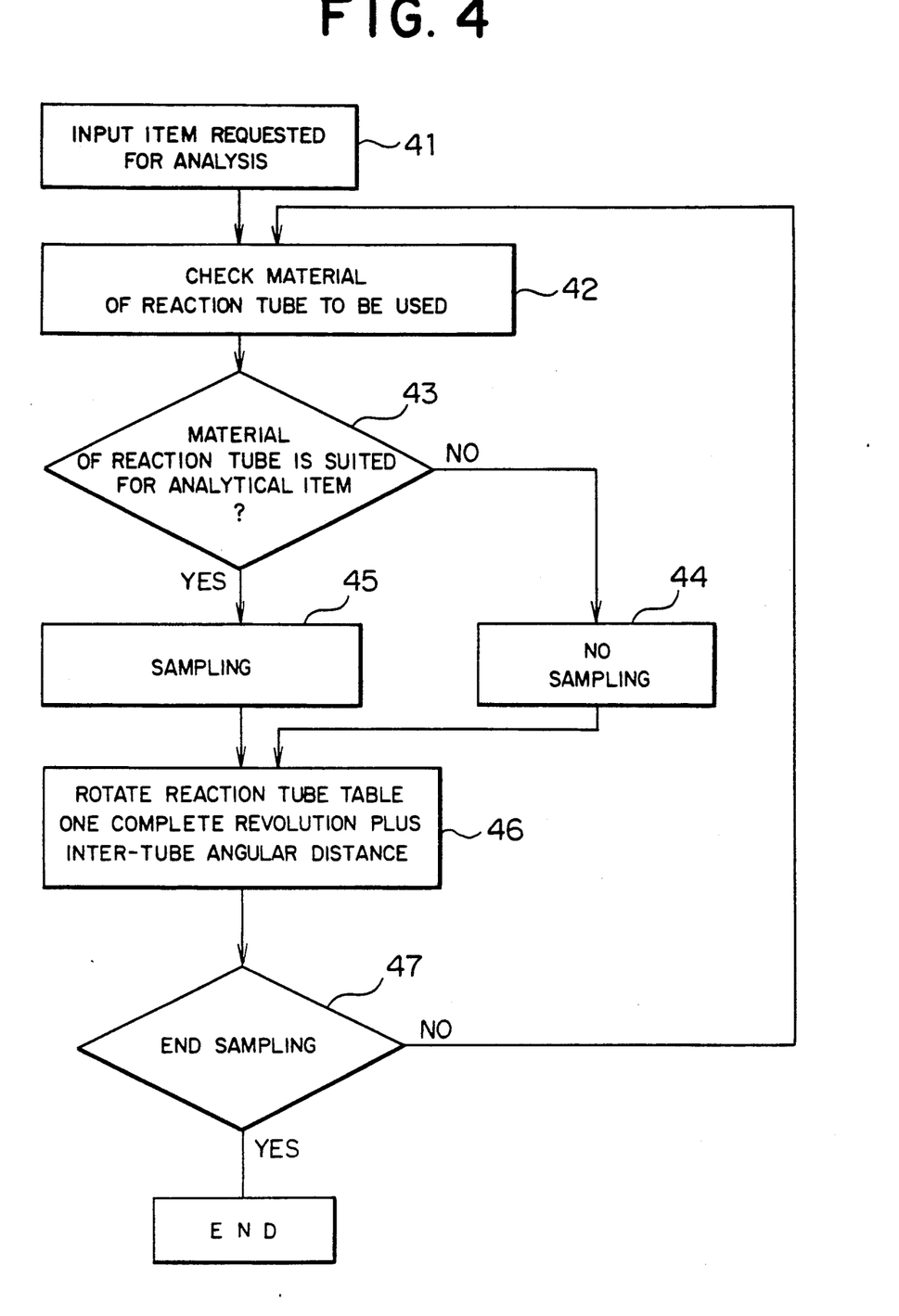
FIG. 4 is a flow chart for illustrating operations of major parts of the analysis apparatus according to the first embodiment of the invention.

Next, referring to FIG. 4, description will be made of operations performed by the computer 17 which constitutes the heart of the control facilities for the automatic analysis apparatus. In response to an analysis request for a certain item in a step 41, the computer 17 consults the table or list shown in FIG. 3 and stored in the memory 17' incorporated in the computer to thereby determine the reaction tube which is suited for or compatible with the item for the analysis as requested (step 42). In a step 43, the computer 17 checks whether or not the reaction tube located at the sample injection position is compatible with or suited for the item for analysis. Since reaction tubes of different materials are arrayed alternately, relations between the angular positions of the reaction table 1 and the reaction tubes arriving at the sample injection position can previously be stored in the memory 17' incorporated in the computer 17 so that the computer can determine the material of the reaction tube arrived at the sampling position. Accordingly, in a step 43, it is checked on the basis of the above-mentioned relations whether the material of the reaction tube determined at the step 42 coincides with the material of the tube located currently at the sampling or sample injection position read out from the memory. If the result of the decision step 43 is negative (No), no sample is injected (step 44) and the processing proceeds to a step 46. On the other hand, in case the result of the decision step 43 is affirmative (Yes), the sample is pipetted into the reaction tube located at the sampling position in a step 45. Subsequently, the reaction table is rotated one complete revolution plus one inter-tube angular distance in a step 46, which is followed by a step 47 where a decision is made as to whether or not the sample pipetting has been completed. When the answer of this decision step 47 is affirmative, the computer processing now under consideration comes to an end. If otherwise (No), the step 42 is regained, whereupon the operation described above is repeated.

Figure 5:
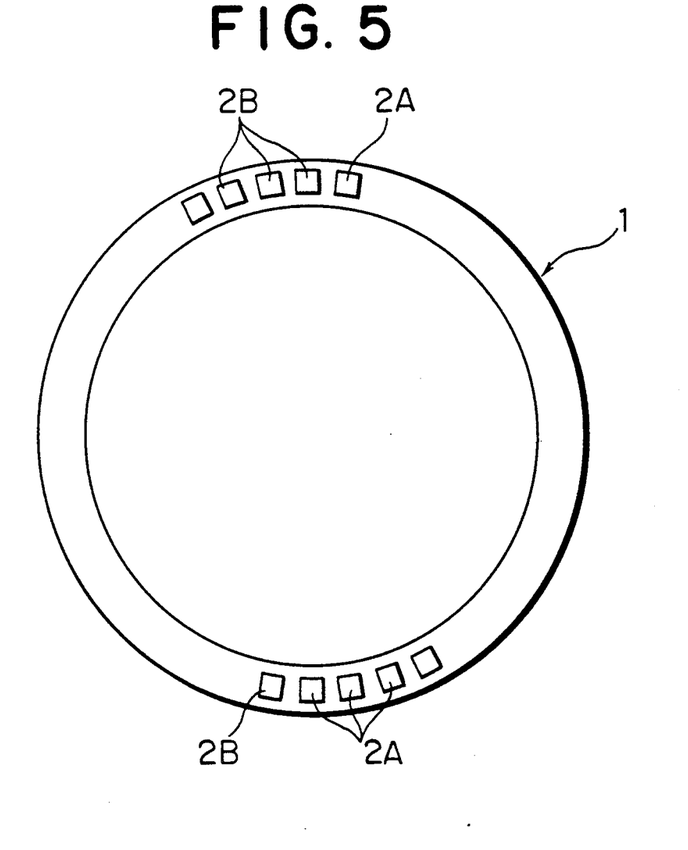
FIG. 5 is a view showing an array of reaction tubes disposed on a reaction table according to another embodiment of the invention.

FIG. 5 is a top plan view showing fragmentally an automatic analyzing apparatus according to another embodiment of the invention. More specifically, this figure shows a top plan view of a modified structure of the reaction table. As can be seen in the figure, the reaction tubes 2A and 2B made of mutually different materials are successively arrayed along two halves of the circumferential edge of the reaction table 1, respectively. That is, a number of the reaction tubes 2A of one material are successively arrayed along a half of the outer peripheral edge of the table 1, while a like number of reaction tubes 2B of another material are successively arrayed along the other half of the circular edge of the table 1. In the case of this embodiment, the one cycle mentioned in connection with the step 46 in FIG. 4 is defined to be a half-rotation plus an inter-tube angular distance. Except for this respect, the operation of the automatic analysis apparatus shown in FIG. 5 is substantially the same as that of the apparatus shown in FIG. 5 and described above by reference to FIG. 4.

Assuming, by way of example, that a given one of the reaction tubes 2A is currently set at the sampling position, then the reaction tube 2B of different material located diametrically opposite to the given reaction tube 2A will arrive at the sampling position after lapse of one cycle. In other words, upon every lapse of one cycle, the reaction tubes of mutually different materials are alternately brought to the sampling position. To say it another way, although two types of reaction tubes made of mutually different materials are not disposed alternately with each other in a circular array along the circumferential edge of the table 1, the different type reaction tubes which arrive at the sampling position are exchanged from one to another upon every lapse of one cycle defined above, whereby there can be attained substantially the same effects as those of the analysis apparatus described hereinbefore in conjunction with FIGS. 1 and 4. Subsequently, the analyzing operation of the apparatus shown in FIG. 5 is performed in a same manner as that of the apparatus according to the first embodiment.

In conjunction with the automatic analysis apparatus shown in FIG. 5, there may arise a case where the use of three or four different types of reaction tubes is required or desired. In that case, three or four groups of the reaction tubes each containing the same material may be arrayed over arcuate segments each of 120° or 90°, respectively.

In the foregoing, exemplary embodiments of the invention have been described in which the reaction tube to be used is selected in consideration of relations between the materials constituting the tubes and the items for analysis so that adhesion between the tube material and the reagent can positively be prevented. According to the concept incorporated in the embodiment illustrated in FIG. 5, a desired number of different types of reaction tubes can be installed on the reaction table 1 in predetermined arrays, wherein the reaction tube of the material suited for the intended analysis may be selectively determined for carrying out the analysis.

According to another aspect of the invention, there is provided an automatic analysis apparatus for clinic examination which comprises a reaction tube container for accommodating therein a number of different type reaction tubes made of materials differing from one another, and a reaction tube transferring mechanism for taking out a given reaction tube from the tube container and disposing it at a predetermined reaction tube setting position. In other words, in place of disposing a plurality of reaction tubes of different material along the reaction line, a reaction tube of a material suited for the item for analysis as designated is taken out from the tube container and placed at the reaction tube setting position provided on the reaction line along which operations involved in the reaction and analysis are successively carried out. The used reaction tube is taken out from the reaction line.

Next, another embodiment incorporating the above-mentioned aspect of the invention will be described by reference to the drawings. According to the instant embodiment shown in FIG. 6, cartridges 31 and 32 each accommodating a number of reaction tubes of a specific material are provided while a reaction table 33 is formed with a number of holes 33a formed along the circumferential edge thereof for receiving therein the reaction tubes, respectively, in place of the reaction tubes of mutually different materials disposed previously on the reaction table as described hereinbefore.

Figure 6:
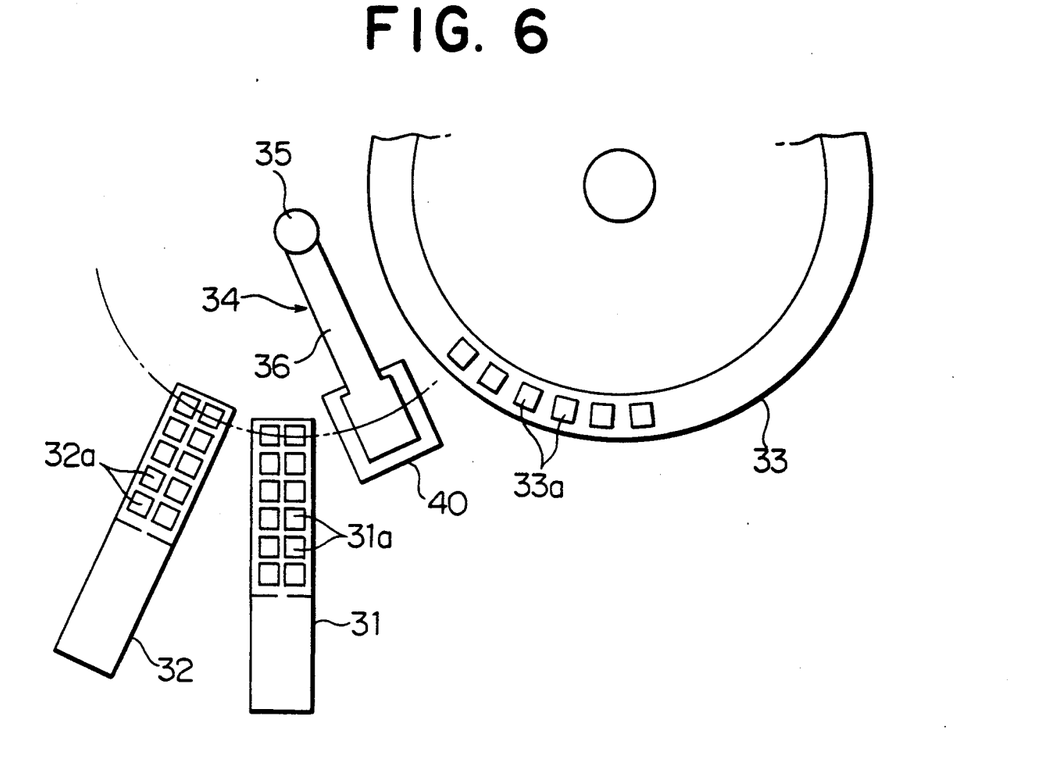
FIG. 6 is a plan view showing a major portion of an automatic analysis apparatus according to yet another embodiment of the invention.

The reaction tubes accommodated in the cartridge 31 differ from those contained within the cartridge 32 with respect to the tube material. By way of example, the reaction tube 31 may be formed of an acrylic resin while the reaction tube 32a contained in the cartridge 32 may be made of glass.

Figure 7:
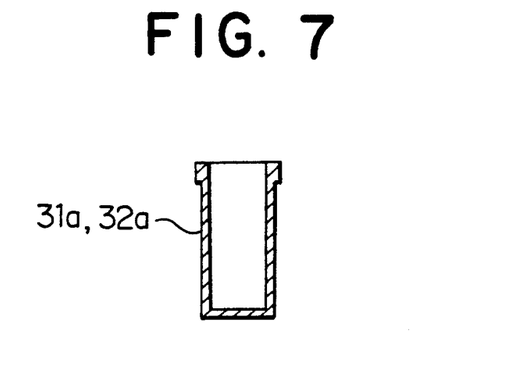
FIG. 7 is a view showing a vertical section of a reaction tube used in the apparatus shown in FIG. 6.
Figure 8:
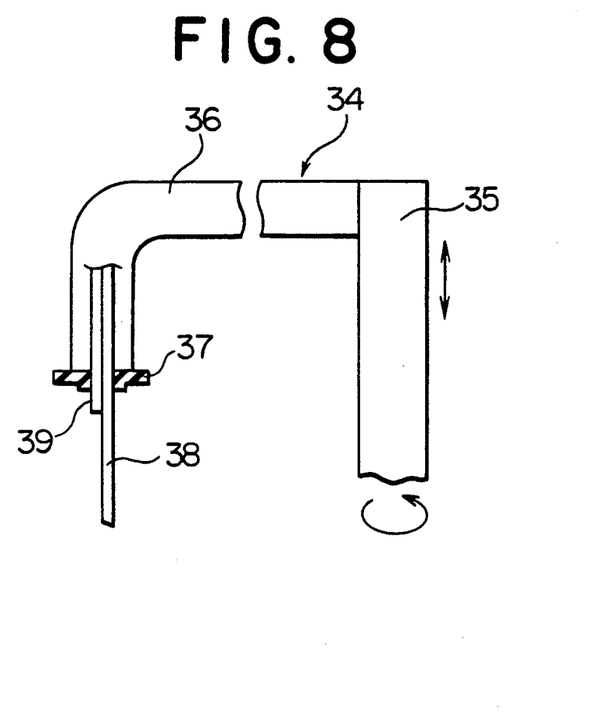
FIG. 8 is a partially sectioned side elevational view showing a reaction tube transfer mechanism in the automatic analysis apparatus shown in FIG. 6.

FIG. 7 shows a vertical section of the reaction tube 31a or 32a. Disposed between the cartridges 31 and 32 and the reaction table 33 is a reaction tube transfer mechanism 34 for transporting the reaction tube. As can be seen in FIG. 8, this transfer mechanism 34 is composed of a shaft 35 mounted rotatably and vertically movably, an arm 36, a cover 37 made of rubber for plugging a top open end portion of the reaction tube, a nozzle 38 for evacuating air from the reaction tube through suction, a nozzle 39 for charging air into the reaction tube and a tube wastebasket 40 in which the used reaction tubes are discarded.

Figure 9A:
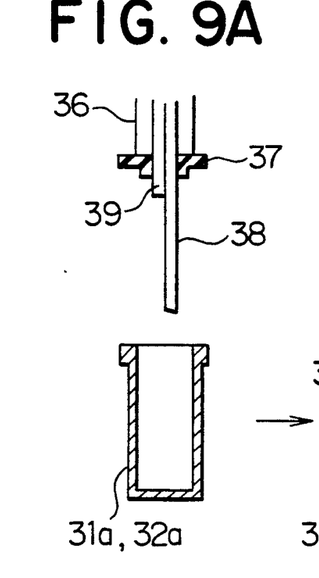
FIGS. 9A, 9B and 9C are views for illustrating operations of the reaction tube transfer mechanism in the analysis apparatus shown in FIG. 6.
Figure 9B:
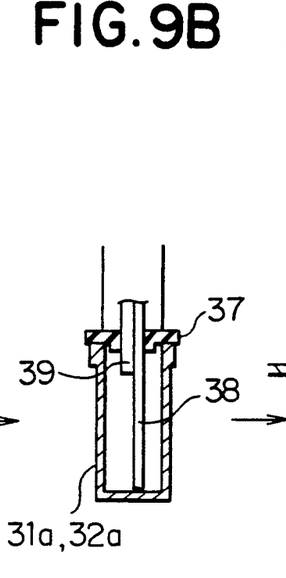

Next referring to FIGS. 9 and 10, description will be made of an operation for transferring the reaction tube 31a or 32a from the cartridge 31 or 32 to the reaction table 33 and placing the tube in a predetermined cavity or hole formed in the table 33. In a step 102, the transfer mechanism 34 is actuated and stopped at a position where the nozzle assembly is disposed above the reaction tube which is to be taken out from the cartridge (FIG. 9A), whereupon the shaft 35 is moved downwardly so that the nozzle 38 moves toward the reaction tube until the tip end portion of the evacuating nozzle 38 has been fully inserted into the interior of the reaction tube 31a (or 32a). In this state, the top open end portion of the reaction tube 31a remains closed by the rubber cover 37 (FIG. 9B).

Next, in a step 103, the air is evacuated from the reaction tube through the suction nozzle 38. As a result of this, the air is exhausted from the reaction tube, whereby the cover 37 is brought to air-tight contact with the top open end of the reaction tube (FIG. 9B). Subsequently, in a step 104, the arm 36 having the reaction tube mounted at the free end thereof under suction is moved upwardly to a predetermined height and stopped, which is then followed by a step 105 where the arm 36 is rotated for a predetermined angular distance to a position located above the wastage tube basket 40. In a step 106, air is charged into the reaction tube through the nozzle 39 to thereby cause the tube to drop into the wastebasket 40.

Figure 9C:
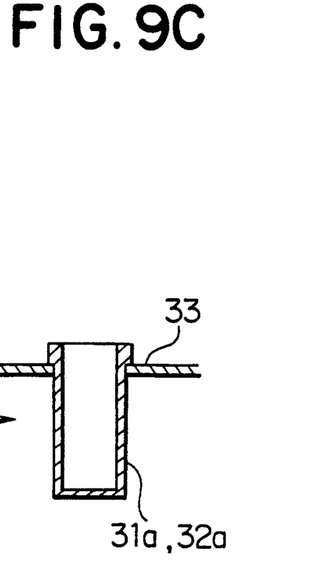

Subsequently, in a step 107, the arm 36 is moved to a position above the cartridge 31 and 32 in which the selected reaction tube is contained. In a step 108, the nozzle 38 is inserted into the selected reaction tube by lowering the arm until the cover 37 is brought into contact with the reaction tube. Subsequently, the air is evacuated from the selected reaction tube through the nozzle 38. In a step 110, the arm holding the selected reaction tube is moved upwardly and stopped at a predetermined vertical position. In a next step 111, the arm 36 is rotated horizontally to a position at which the reaction tube held by the arm is located above the cavity 33a in which the reaction tube is to be placed. The arm is then moved downwardly until the reaction tube has been inserted within the hole or cavity 33a. In this state, the air is charged into the reaction tube through the air injection nozzle 39 (step 113), as a result of which the cover 37 is removed and the reaction tube 31a as transferred is installed on the reaction table 33 (FIG. 9C). Thereafter, the arm 36 of the tube transfer mechanism 34 is moved upwardly away from the reaction table 33.

Figure 10:
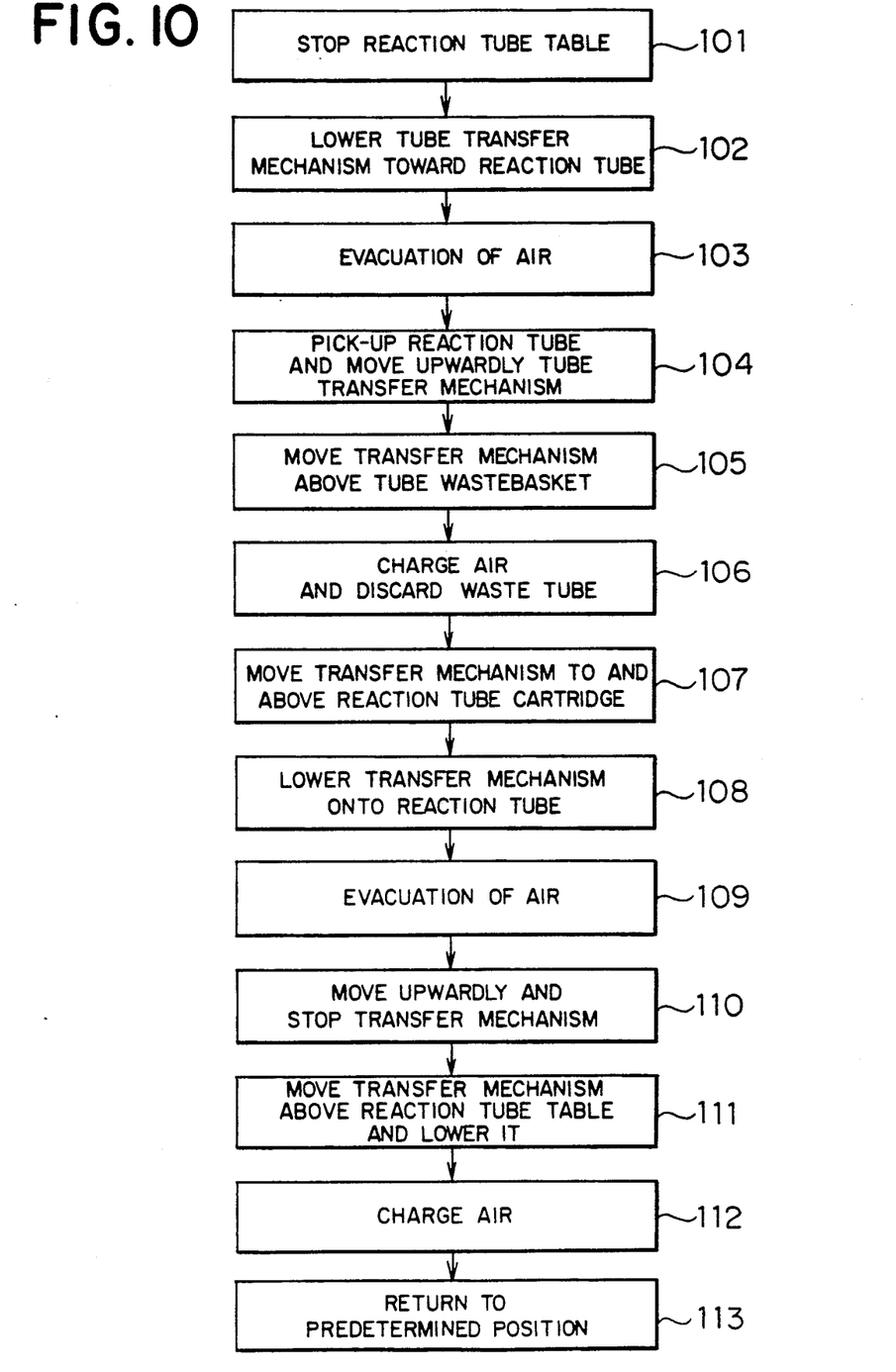
FIG. 10 is a flow chart for illustrating in more detail the operations of the reaction tube transfer mechanism.

FIG. 10 is a flow chart for illustrating the operation of the tube transfer mechanism 34.

Figure 11:
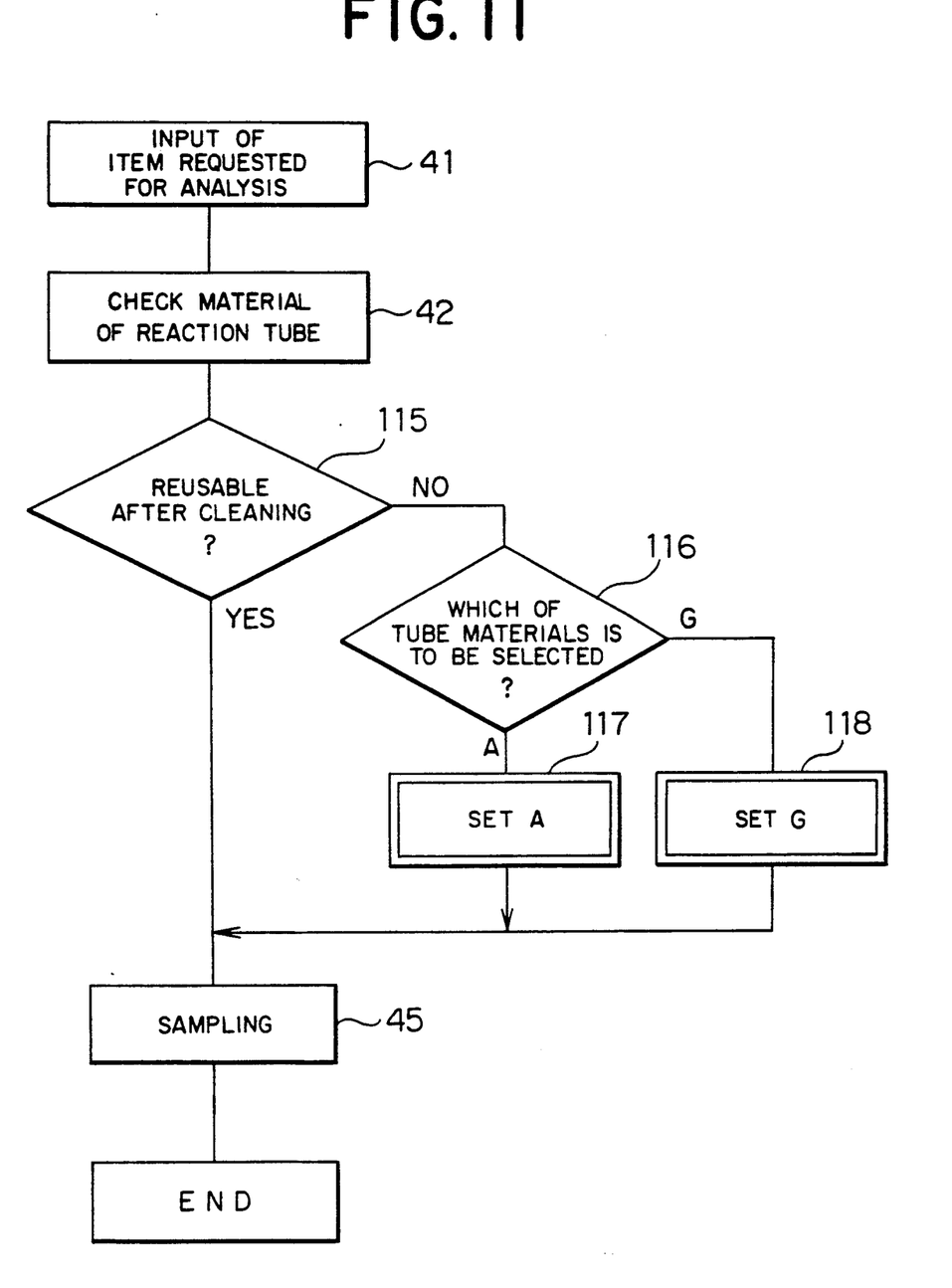
FIG. 11 is a flow chart for illustrating a routine of operations performed by the analysis apparatus shown in FIG. 6.

Next, description will turn to the sampling operation in the automatic analysis apparatus for the clinic application according to the instant embodiment. In FIG. 11, the steps designated by same reference symbols as those used in FIG. 4 represent same or like operations performed in the corresponding steps. Accordingly, repeated description of these steps will be unnecessary.

Referring to FIG. 11, the material of the reaction tube is checked at a step 42. Thereafter, in a step 115, it is checked whether or not the reaction tube disposed at the sampling position can be reused after cleaning. If the answer of this decision step 115 is affirmative (Yes), the processing proceeds to a sampling step 45. If otherwise (No), a step 116 is executed to decide which of the reaction tubes contained in the two cartridges 31 and 32 and made of mutually different materials is to be selected. This decision can be effectuated in a similar manner as described hereinbefore.

When a reaction tube of acrylic resin is selected in the step 116, the processing proceeds to a routine A while upon selection of the glass-made reaction tube, a routine G is enabled. In either case, the operation shown in the flow chart of FIG. 10 is executed in a step 117 or 118. Thereafter, the sampling is performed in a step 45, whereupon the processing comes to an end.

After the reaction table has been equipped with the reaction tube, the former is operated in the manner described hereinbefore, whereby the pipetting of the sample into the reaction tube, mixing, and light absorbance measurement of the reactant liquid are performed. Upon completion of the measurement, the reaction tube is cleaned. Thereafter, it is decided whether or not the reaction tube can be used in a subsequent analysis. This decision can be made on the basis of the item for analysis by checking whether or not there is a possibility of the succeeding analysis being affected by adhesion of the reagent. When the possibility of adhesion is decided, another reaction tube of a material differing from that of the used tube is selected.

In that case, the nozzle assembly of the transfer mechanism 34 is moved to insert the nozzle into the used reaction tube to hold it under suction. In this state, the used reaction tube is carried to a position located above the wastage tube basket 40, whereupon the air is charged into the used tube through the nozzle 39 to release the tube and cause it to drop into the wastebasket 40. Thereafter, the arm 36 of the transfer mechanism 34 is rotationally moved to the position of the cartridge which contains the reaction tube of another material which is compatible with the item for analysis, whereupon suction of the desired tube, transportation and setting on the reaction table 33 are performed in a similar manner as described previously.

There are formed in the reaction table 33 a plurality of holes 33a, each of which can accommodate a reaction tube. Thus, the analyses can be carried out successively by making use of the individual holes 33a.

The reaction tubes 31a and 32a within the cartridges 31 and 32 shown in FIG. 6 are resiliently urged to move in one direction invariably under the influence of respective springs. Accordingly, when a leading reaction tube is taken out from the cartridge 31 or 32, the remaining ones are forced to move successively toward the position where the tube taken out was located. Further, the individual reaction tubes within each cartridge may be juxtaposed in two rows, as shown in FIG. 6. In that case, the angles of rotation of the arm 36 may previously be stored in the memory incorporated in the computer in association with the reaction tube rows so that when one of the tube rows becomes empty, the reaction tube can be taken out from the other row or alternatively the reaction tubes may be taken out alternately from the two rows. Of course, the reaction tubes may be arrayed in a single row within each cartridge.

The automatic analysis apparatus described just above is so arranged that each of the two cartridges 31 and 32 is adapted to accommodate therein a plurality of reaction tubes of the same material, wherein the material of the reaction tubes accommodated within one cartridge differs from that of the tubes contained in the other cartridge. It should, however, be mentioned that such an arrangement can equally be adopted in which a plurality of reaction tubes of mutually different materials are accommodated within one cartridge. In that case, the reaction tube transfer mechanism should be imparted with a function for identifying discriminatively the reaction tubes for allowing the selection thereof. To this end, each reaction tube may be printed with a bar code or provided with a number of small projections or dimples, wherein the bar code or the number of projections or dimples may be made to differ from one tube to another so as to make it possible to identify the materials of the tubes. Such bar codes, projections or dimples can be detected by utilizing any appropriate sensor techniques known in the art.

As will be appreciated from the foregoing description, the automatic analysis apparatuses according to the invention are implemented with such structure that the reaction tube of the material suited optimally for the analysis to be performed on a given sample can be selected. Thus, adhesion of the reagent to the reaction tube and other unwanted phenomena can be avoided, whereby analyzed data can be obtained with higher accuracy. Further, by automating the selection of the suitable reaction tube, the clinical examiner can save labor and time for manually exchanging the reaction tubes in dependence on the items for analysis. Further, the time taken for making available the result of the analytical measurement can be shortened. Additionally, errors due to the false selection of the reaction tube can be reduced.

I claim:

1. An automatic analysis apparatus for clinical examination, comprising:
   sample holding means for holding a plurality of samples;
   reagent holding means for holding a plurality of reagents;
   a reaction tube holding unit for holding reaction tubes to conduct reactions between said samples and said reagents;
   input means for inputting analytical items for the respective samples;
   a sample pipetting unit for pipetting one of said samples into one of said reaction tubes;
   a reagent pipetting unit for pipetting one of said reagent into said one reaction tube;
   a mixing unit for mixing the sample and the reagent pipetted into said reaction tube;
   a light intensity measuring unit for measuring absorbance of a reactant liquid within said reaction tube;
   a reaction tube cleaning unit for discharging the reactant liquid from said reaction tube and cleaning said reaction tube; and
   a control unit for controlling operations of the automatic analysis apparatus as a whole;
   wherein said reaction tube holding unit includes means or holding plural types of reaction tubes, said plural types of reaction tubes including at least one reaction tube made of a different material than at least one other reaction tube; and
   wherein said control unit includes selecting means for selecting a reaction tube form said plural types of reaction tubes based on the type of material of said selected reaction tube, the selected reaction tube being made of a material to which one of said reagents to be used for one of said analytical items of a sample as inputted through said input means does not adhere after cleaning by said reaction tube cleaning unit.

2. An automatic analysis apparatus according to claim 1, wherein said reaction tube holding unit includes a sample table on which said plural types of reaction tubes of different materials are disposed in a substantially alternate array.

3. An automatic analysis apparatus according to claim 2, wherein reaction tubes disposed on said sample table include reaction tubes of at least two different materials.

4. An automatic analysis apparatus according to claim 1, wherein said reaction tube holding unit includes a sample table having a same number of partitioned compartments as the number of types of said reaction tubes of different materials, and wherein the reaction tubes are segregated by type so that all reaction tubes of a common type are arrayed within a single one of said compartments.

5. An automatic analysis apparatus according to claim 1, wherein said selecting means includes a memory for storing a list containing data representing relations between items for analysis and reaction tubes of materials to which said items for analysis do not adhere after the reaction tubes are cleaned by said reaction tube cleaning unit, means for searching for one of said reaction tubes the material compatible with the time for analysis inputted by consulting said list for a reaction tube to which the item for analysis does not adhere after cleaning, and reaction tube setting means for setting the reaction tube determined by said search means at a predetermined position.

6. An automatic analysis apparatus according to claim 5, wherein said reaction tube setting means includes driving means for driving said reaction tube holding unit such that the reaction tube determined by said search means is disposed at a predetermined position.

7. An automatic analysis apparatus according to claim 5, wherein said reaction tube setting means includes a reaction table having a plurality of receptacles for receiving therein the reaction tubes, a reaction tube accommodating container for accommodating therein the plural types of reaction tubes, and transfer means for selecting the reaction tube determined by said search means from said reaction tube accommodating container and for transporting the selected reaction tube to a predetermined one of said receptacles provided on said reaction table.

8. An automatic analysis apparatus according to claim 7, wherein said reaction tube accommodating container includes a plurality of cartridges each of which accommodates therein reaction tubes of a common material, while the materials of the reaction tubes differ from one to another one of said cartridges.

9. An automatic analysis apparatus according to claim 8, wherein said transfer means includes means for selecting one of said cartridges accommodating the reaction tube determined by said search means and for transporting the reaction tube disposed within the selected cartridge to a predetermined one of said receptacles provided on said reaction table.

10. An automatic analysis apparatus according to claim 7, wherein said transfer means includes a member capable of contacting hermetically with a top end of said reaction tube, evacuation/charge nozzles secured to said member and extending downwardly through said member, and a driving mechanism for moving said member in vertical and horizontal directions.

11. An automatic analysis apparatus according to claim 10, wherein said control unit includes means for evacuating air from the reaction tube through said nozzle to thereby cause said member to attach the top end of said reaction tube when said reaction tube is to be lifted up and transported, and means for charging air into said reaction tube through said nozzle upon completed transportation of said reaction tube.

12. An automatic analysis apparatus according to claim 1, wherein said selecting means further selects the reaction tube based on the reagent to be used for the analytical item of the sample as inputted through said input means.

* * * * *